(12) United States Patent
Farag et al.

(10) Patent No.: US 6,559,099 B1
(45) Date of Patent: May 6, 2003

(54) METHODS FOR ENHANCING PLANT HEALTH, PROTECTING PLANTS FROM BIOTIC AND ABIOTIC STRESS RELATED INJURIES AND ENHANCING THE RECOVERY OF PLANTS INJURED AS A RESULT OF SUCH STRESSES

(75) Inventors: Karim Farag, Al-Ain (AE); Jiwan P. Palta, Madison, WI (US); Stephen B. Ryu, Kwangju (KR)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/538,423

(22) Filed: Mar. 29, 2000

(51) Int. Cl.$^7$ .............................................. A01N 57/12
(52) U.S. Cl. ...................................... 504/194; 504/201
(58) Field of Search ................................. 504/194, 201

(56) References Cited

U.S. PATENT DOCUMENTS

| | | | | |
|---|---|---|---|---|
| 4,117,168 A | | 9/1978 | Ecke .......................... | 424/337 |
| 4,576,626 A | * | 3/1986 | Bauer et al. .................... | 71/28 |
| 4,645,682 A | | 2/1987 | Elmore .......................... | 427/4 |
| 4,834,899 A | | 5/1989 | Klevecz ........................ | 252/70 |
| 4,990,351 A | | 2/1991 | Orman et al. ................ | 426/333 |
| 5,110,341 A | | 5/1992 | Palta et al. ..................... | 71/86 |
| 5,126,155 A | | 6/1992 | Palta et al. .................. | 426/331 |
| 5,468,737 A | | 11/1995 | McAnalley et al. .......... | 514/54 |
| 5,516,667 A | | 5/1996 | Nishizawa ............... | 435/172.3 |
| 5,521,223 A | | 5/1996 | Piazza et al. ............... | 514/785 |
| 5,681,829 A | | 10/1997 | Tempesta et al. ............. | 514/78 |
| 5,720,980 A | | 2/1998 | Cohen ........................ | 424/523 |
| 5,922,649 A | * | 7/1999 | Pehu et al. .................. | 504/320 |

FOREIGN PATENT DOCUMENTS

| | | |
|---|---|---|
| DE | 277 831 A | 4/1990 |
| EP | 0 068297 A | 1/1983 |
| JP | 930192425 | 8/1993 |
| JP | 06 234609 A | 8/1994 |
| JP | 07 048218 A | 2/1995 |
| SU | 87372490 | 12/1987 |
| WO | WO99/23889 A | 5/1999 |
| WO | WO99/25191 A | 5/1999 |

OTHER PUBLICATIONS

Farag, Karim, M., et al., "Use of Lysophosphatidylethanolamine, a natural lipid, to retard tomato leaf and fruit senescence"*Physiol. Plant* 87:515–524 (1993) XP–002104454.

Farag, Karim, M., et al., "Use of Natural Lipids to Accelerate Ripening and Enhance Storage Life to Tomato Fruit with and without Ethephon" *HortTechnology*, 3(1):62–65 (Jan./Mar. 1993) XP–002104455.

Ryu, Stephen B., et al., "Expression of Phospholipase D during Castor Bean Leaf Senescence", *Plant Physiol.* 108:713–719 (1995).

Ryu, Stephen B., et al., "Inhibition of phospholipase D by lysophosphatidylethanolamine, a lipid–derived senscence retardant" *Proc. Natl. Acad. Sci. U.S.A.* 94:12717–12721 (1997).

Kaur, Navjot et al., Postharvest Diping Natural Lipid, Lysophosphatidylethanolamine, May prolong Vase Life of Snapdragon Flowers, *HortScience*, 3265:888–890 (1997).

International Search Report dated Dec. 13, 2001 for PCT/US01/09766.

* cited by examiner

*Primary Examiner*—S. Mark Clardy
(74) *Attorney, Agent, or Firm*—Wood, Phillips, Katz, Clark & Mortimer

(57) ABSTRACT

The present invention relates to a method of enhancing the health of plant or seed in order to protect a plant or a seed from a stress-related injury by treating a plant with a composition containing at least one lysophospholipid. The present invention further relates to a method of enhancing or accelerating the recovery of an injured plant by treating such injured plant with a composition containing at least one lysophospholipid. Finally, the present invention relates to a method of enhancing the germination of seeds and seedling vigour by treating seeds with a composition containing at least one lysophospholipid.

25 Claims, 3 Drawing Sheets

(3 of 3 Drawing Sheet(s) Filed in Color)

dH20          LPE

ETHREL        ETHREL + LPE

LPE dH2O dH2O LPE

METHODS FOR ENHANCING PLANT HEALTH, PROTECTING PLANTS FROM BIOTIC AND ABIOTIC STRESS RELATED INJURIES AND ENHANCING THE RECOVERY OF PLANTS INJURED AS A RESULT OF SUCH STRESSES

This invention was made with no United States government support.

FIELD OF THE INVENTION

The present invention relates to a method of enhancing plant or seed health in order to protect plants or seeds from stress-related injuries. Additionally, the present invention relates to a method of enhancing or accelerating the recovery of plants suffering from stress-related injuries. Finally, the present invention relates to a method of enhancing the germination of seeds and seedling vigour.

BACKGROUND OF THE INVENTION

The yield and quality of desired plant products is determined by the health of the plant. A healthy plant is one which is able to withstand biotic (pathogens, insects, etc.) stresses as well as abiotic (cold, heat, drought, etc.) stresses. Conversely, a weak plant is one which succumbs to pathogen and/or environmental stresses. During imbibation, dry seed experiences stresses due to sudden rehydration. These stresses can impact both the extent and speed of seed germination. A healthy seed is one which is able to germinate faster and thus get a head start. Such a head start improves the seed's chances of increasing its yield, especially in areas with shorter growing seasons. The commercial value of seed is determined in part on percentage (%) germination, rate of germination and the robustness of the seedling produced. There is a great interest in improving these properties of commercial seeds.

Mature seeds of most crop plants contain very little moisture. These seeds can be stored for a long time in dormant stage. The living portion of the seed, the embryo, remains inactive in dehydrated state as long as the seed is remains dry. When these seeds are sown in the soil a rapid rehydration occurs. During this process, the embryo cells rehydrate and expand. Cell membranes are assembled into an organized structure that preserves the integrity of the cells. However, since rehydration is generally quick, the cell membrane is not fully assembled in the initial phase of rehydration. This results in some leakage of cellular contents. During rehydration, since membranes are 'leaky'. Important molecules, including proteins, carbohydrates and inorganic molecules, are known to leak in the initial phase of rehydration. This leakage of important cellular constituents is known to cause injury or stress to the embryo. Leakage of cellular constituents has been associated with the failure of seeds of many crops plants to germinate and/or produce healthy seedlings. Many seeds fail to germinate if the leakage of cellular solute is significant. "Seed priming" is intended to impart "health" to the embryo cells so that leakage (thereby injury) to the embryo can be minimized.

The injury of crops as a result of abiotic and biotic stresses has been a major problem in the agricultural production areas of the U.S. Specifically, over 60% of the crop loss for last 50 years has been due to abiotic stresses (see USDA Agricultural Statistics, 1998). Abiotic stresses include chilling, freezing, drought, heat, and other environmental factors. In 1996, the loss of crop yield due to abiotic stresses was recorded to be more than a billion dollars in the U.S. (see USDA Agricultural Statistics, 1998). Thus, there is a tremendous interest in the plant industry to find a technology that can be used to prevent or mitigate stress injury and to accelerate recovery following a stress injury.

Lysophospholipids are derived from membrane phospholipids by the removal of a fatty acid by the action of an enzyme phospholipase A2. Lysophospholipids are naturally present in plant and animal tissues, and can be found in high concentrations in egg yolk, brain tissue, and soybeans. Lysophospholipids are available commercially from Avanti Polar Lipids, Inc. (Alabaster, Alabama) and from Sigma Chemical Co. (St Louis, Mo.). Lysophospholipids, such as lysophosphatidylethanolamine (hereinafter referred to as "LPE") and lysophosphatidylinositol (hereinafter "LPI"), have been exploited for accelerating fruit ripening, enhancing fruit stability during storage, and increasing the shelf life by retarding senescence of plant tissues such as fruits, vegetables, and cut-flowers. Farag, K. M. et al., *Physiol. Plant*, 87:515–524 (1993), Farag, K. M. et al., *HortTech.*, 3:62–65 (1993), Kaur, N., et al., *HortScience*, 32:888–890 (1997), Ryu, S. B., et al., *Proc. Natl. Acad. Sci. USA*, 94:12717–12721 (1997). Methods for using LPE to enhance fruit ripening and storage stability are disclosed in U.S. Pat. Nos. 5,126,155 and 5,100,341. Methods for using LPE with 18:1 fatty acid and LPI to retard senescence and to enhance fruit ripening is described in WO 99/23889.

SUMMARY OF THE INVENTION

The present invention relates to a method of enhancing plant or seed health in order to prevent injuries to a plant or seed upon exposure to a stress. The method involves applying to a plant or seed before exposure to a stress, an effective amount of a composition containing at least one lysophospholipid(s) and optionally, at least one activating agent. The preferred lysophospholipids contained in the composition are LPE and LPI.

Additionally, the present invention further relates to a method of enhancing the recovery of a plant injured as a result of stress. The method involves applying to a plant after exposure to stress, an effective amount of a composition containing at least one lysophospholipid(s) and optionally, at least one activating agent. The preferred lysophospholipids contained in the composition are LPE and LPI.

Finally, the present invention relates to a method of enhancing the germination of seeds. The method involves treating seeds with a composition containing at least one lysophospholipid(s) and optionally, at least one activating agent. The preferred lysophospholipids contained in the composition are LPE and LPI.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

DETAILED DESCRIPTION OF THE INVENTION

In one embodiment, the present invention relates to a method of enhancing plant health in order to protect a plant or a seed from stress-related injuries upon exposure to one or more stresses. In a second embodiment, the present invention relates to a method of enhancing or accelerating the recovery of an injured plant after exposure to a stress. Each of these methods involves applying to a plant or a seed, either before and/or after exposure to a stress, a composition containing at least one lysophospholipid(s) and optionally, at least one activating agent. In a third embodiment, the present invention relates to a method of enhancing germination of seed. This method involves treating seed with a composition containing at least one lysophospholipid(s) and optionally, at least one activating agent.

As used herein, the term "stress injury" refers to an injury resulting from an abiotic and/or a biotic stress. As used herein, the term "abiotic stress" refers to those non-living substances or environmental factors which can cause one or more injuries to a plant. Examples of abiotic stresses include those injuries which result from chilling, freezing, hail, flooding, drought, soil compaction, soil crusting and agricultural chemicals such as pesticides and herbicides. For seeds, rapid rehydration during the initial phase of seed germination is considered to be an abiotic stress. As used herein, the term "biotic stress" refers to those living substances which cause one or more injuries to a plant. Examples of biotic stresses include those injuries resulting from infections by insects, nematodes, snails, mites, weeds, pathogens, such as fungus, bacteria or viruses, and physical damage caused by people and animals (i.e. grazing, tredding, etc.).

As used herein, the term "plant" refers to a whole live plant as well as to any part, tissue or organ from a live plant. For example, the term "plant" includes fruit, flowers, tubers, roots, stems, hypocotyls, leaves, petioles, petals, seeds, etc. The plants of the present invention may be planted in the terra firma, such as a field, garden, orchard, etc., or may be in a pot or other confined growing apparatus (such as a window box, etc.).

As discussed above, the methods of the present invention employ a composition containing at least one lysophospholipid and optionally, at least one activating agent. Additionally, the composition of the present invention may contain combinations of a number of lysophospholipids and activating agents.

As used herein, the term "lysophospholipids" refers to derivatives of phospholipids having a single fatty acid removed. Specifically, the lysophospholipids contained in the composition have the formula:

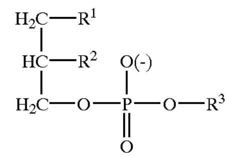

wherein $R^1$ is selected from the group consisting of $C_5$–$C_{22}$ acyloxy and $C_5$–$C_{22}$ alkoxy group; $R^2$ is selected from the group consisting of hydrogen, hydroxyl, $C_1$–$C_5$ acyloxy and $C_1$–$C_5$ alkoxy group; and $R^3$ is selected from the group consisting of hydrogen, choline, ethanolamine, glycerol, inositol and serine, wherein $R^1$ and $R^2$ are interchangeable.

Examples of lysophospholipids having the above formula and which can be used in the composition include LPE, LPI, LPC, LPG, LPS, LPA and combinations thereof (LPC=Lysophosphatidyl choline; LPG=Lysophospatidyl gycerol; LPS=Lysophatidyl serine; and LPA=Lysophosphatidic acid).

Preferably, the composition contains an acceptable carrier for the lysophospholipids, such as water. However, other carriers, such as organic solvents, can also be used. The amount of lysophospholipid(s) contained in the composition is an amount which is effective to prevent injury from a stress and/or enhance or accelerate the recovery of a plant or a seed after exposure to said stress. Preferably, the amount of lysophospholipid in the composition is in the range of from about 1.0 to about 400 mg per 1 liter of the composition according to the plant treated.

In addition to containing the lysophospholipids, the composition may optionally contain one or more activating compounds. As used herein, the term "activating compounds" refers to agents that enhance wettability, uptake and effectiveness of an active ingredient. In the composition, the active ingredient is the lysophospholipid(s). Examples of activating compounds that can be used in the method of the present invention include ethanol, TERGITOL® (TERGITOL® is a nonylphenol polyoxyethylene ether. TERGITOL® is a registered Trademark of Union Carbide Chemicals and Plastics Company, Inc., available from Sigma Chemical Company, St. Louis, Mo.) and SYLGARD® 309 (SYLGARD® 309 is 76% siloxylated polyether and 24% of a surfactant mixture. SYLGARD® is a registered trademark and SYLGARD® 309 is available from Dow Corning Co., Midland, Mich.). The activating compounds can be present in the composition in the amount of from about 0.05% to about 5% (v/v) of the composition.

The composition can be applied to the plant in any form. Preferably, the composition is applied as spray or simply dipping the plant in the solution.

The composition described herein can be applied to a plant or a seed any time prior to the time the plant or a seed is exposed to a stress injury. Preferably, the plant is treated with the composition at least one hour prior to exposure to a stress injury.

Additionally, the composition described herein can be applied to a plant which has been exposed to a stress injury in order to enhance or accelerate the recovery of such injured plant. As used herein, the term "enhancing recovery" means that the plant is able to reverse the effects of the stress injury faster and more efficiently than a non-treated plant. The composition can be applied to a plant any time after injury has occurred. Preferably, the composition is applied to the plant immediately after the injury to the plant occurs.

The present invention also relates to a method of enhancing germination of seed. The method involves treating seed with the composition described hereinbefore for a period of time of from about 15 minutes to about 5 hours. Preferably, the seed is soaked in the composition described herein for 2 hours. After seeds are treated with the composition they may either be planted or dried and stored using techniques known in the art. Prior to planting, the treated and dried seeds are preferably rehydrated in water or the composition may also contain an activating agent allowed to imbibe water in order to facilitate germination. The seeds may then be planted using techniques known in the art.

By way of example, but not limitation, examples of the present invention shall now be given.

EXAMPLE 1

Protection of Chilling Injury and Enhancement of Recovery

Example 1a

Figure 1A:
FIG. 1A and FIG. 1B show LPE protection of tomato plants from a chilling injury when said plants are sprayed with LPE about 1 hour prior to chilling.

Tomato Plants cv. H9144 (cultivar of Heinz Co.) were grown in 20-liter pots containing peat-lite mix (Readi-earth, Scotts, Marysville, Ohio) in a greenhouse which was supplied with additional tungsten light for a 16 hour photoperiod. One month-old tomato seedlings were sprayed to the point that solution started to run off the leaves with 200 mg/L of LPEegg (LPE extracted from egg) solution 1 hour before or right after chilling. Control leaf branch was sprayed with distilled water. The LPE solution was prepared by suspending 200 mg of crude LPEegg (Avanti Polar Lipids, Inc., Alabaster, Ala.) in one liter of distilled water and then sonicating for 1 minute before spraying. After 4 days of chilling treatment at 4/2° C. day/night temperatures and a 16 hour photoperiod with 200 $\mu$mol m$^{-2}$ s$^{-1}$ fluorescent light intensity, plants were transferred to a growth chamber maintained at 24/18° C. day/night temperatures and a 16 hour photoperiod with 400 $\mu$mol m$^{-2}$ s$^{-1}$ of fluorescent light intensity. As shown in the photograph in FIG. 1A, water-sprayed leaf branches (control) showed severe chilling damage (leaf yellowing and death) and no shoot growth indicating chilling injury in the growing point of the shoot (meristem). Whereas, LPE-treated leaf branch showed mitigation of chilling damage to the leaves and exhibited enhanced shoot meristem growth compared to the control. When measured 10 days after chilling, LPE-sprayed leaf tissues, either before or after chilling, had higher levels of water, chlorophyll, and phospholipid content than water-sprayed control (see Table 1 below). All these measurements demonstrate protection of chilling injury by LPE. FIG. 1A shows LPE protection of chilling injury when LPE was sprayed 1 hour before chilling.

TABLE 1

| Treatment | Leaf Water (fresh/dry wt ratio) Mean ± SE | Leaf Chlorophyll (mg/g dry wt) Mean ± SE | Leaf Phospholipids (nmol/mg dry wt) Mean ± SE |
| --- | --- | --- | --- |
| Experiment 1. When plants were sprayed right after chilling. | | | |
| Water | 9.57 ± 1.0 | 16.5 ± 4.0 | 18.0 ± 3.0 |
| LPE (200 mg/L) | 10.81 ± 0.5 | 28.2 ± 4.0 | 25.7 ± 1.0 |
| Experiment 2. When plants were sprayed 1 hour before chilling. | | | |
| Water | 9.13 ± 0.2 | 13.5 ± 0.1 | 23.6 ± 1.0 |
| LPE (200 mg/L) | 10.1 ± 0.4 | 21.6 ± 0.1 | 25.9 ± 0.3 |

Example 1b

Figure 1B:
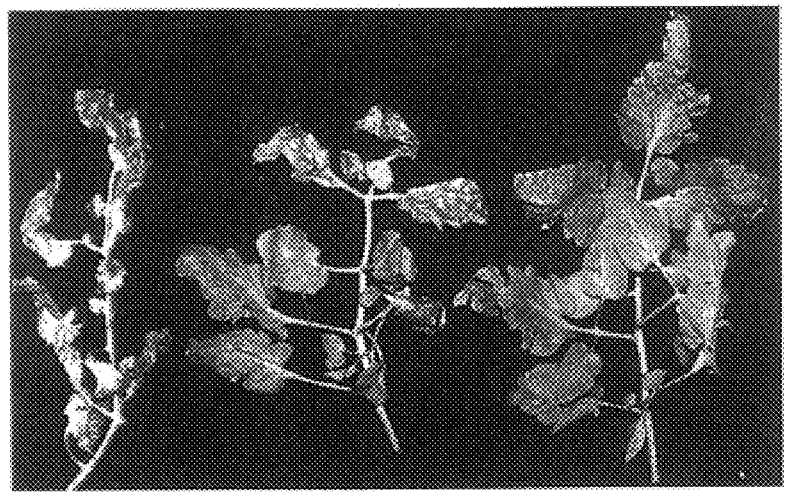

As described above in Example 1a, one month-old tomato seedlings were sprayed either with 100 mg/L of LPEegg, distilled water (sprayed control) or none (non-sprayed control) 1 hour before chilling. Chilling and recovery conditions were the same as in Example 1a above. As shown in FIG. 1B, non-sprayed leaf showed more damage compared to the water-sprayed (control) leaf. This result indicates that while water-spraying itself can mitigate some chilling damage, spraying LPE solution is most effective in protecting the plant from chilling injury.

Example 1c

Figure 1C:
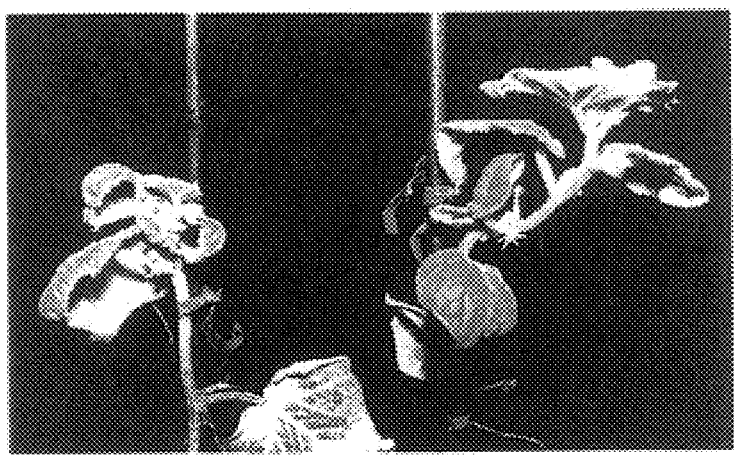
FIG. 1C shows LPE protection of cucumber plants from a chilling injury when said plants are sprayed with LPE about 1 hour prior to chilling.

Cucumber (*Cucumis sativus* inbred line-WI2238) plants were grown in 4 liter plastic pots containing a sterilized mixture of peat:sand:composited soil:field soil (1:1:1:1, v/v) at a greenhouse. Growing conditions and other details were same as in Example 1a. Three week-old cucumber seedlings were sprayed with LPEegg (100 mg/L) twice, 1 hour before chilling and then right after chilling. After 2 days of chilling treatment at the same conditions as in Example 1a, plants were transferred to a growth chamber maintained at 23±2° C. temperature and 16 hour photoperiod with 400 $\mu$mol m$^{-2}$ s$^{-1}$ of fluorescent light intensity. Both control (water-sprayed) and LPE-sprayed plants showed severe chilling damage in leaves but only the LPE-sprayed showed vigorous shoot growth after 7 days indicating recovery of shoot meristem from chilling injury (see FIG. 1C which is a photograph taken 7 days after chilling).

EXAMPLE 2

Protection of Drought Injury and Enhancement of Recovery

Figure 2:
FIG. 2 shows the recovery of vigorous shoot growth in LPE 18:1 sprayed tomato plants compared to water-sprayed plants 7 days after drought stress.

Tomato plants cv. H9478 (cultivar of Heinz Co.) were grown in 20 liter pots and placed in a growth chamber maintained at 24/18° C. day/night temperatures and a 16 hour photoperiod with 400 $\mu$mol m$^{-2}$s$^{-1}$ of cool-white fluorescent lights. Two month-old plants were sprayed with either distilled water, LPEegg (100 mg/L) or LPE 18:1 (100 mg/L) before exposure to drought stress. Drought stress was given by withholding water for 2 days. The plants were sprayed once again with distilled water, LPEegg (100 mg/L) or LPE 18:1 (100 mg/L) right after water was given (alleviation of water stress). During drought stress, all water, LPEegg-and LPE 18:1-sprayed plants were severely wilted but regained turgor soon after water was given again. Control (water-sprayed) plants showed retarded shoot growth, while LPEegg-and LPE 18:1 sprayed leaf showed vigorous shoot growth after 2 or 3 days. FIG. 2 shows vigorous shoot growth in a LPE 18:1-sprayed plant but poor shoot growth in a water-sprayed plant 7 days after drought stress was alleviated.

EXAMPLE 3

Protection of Pesticide-injury and Enhancement of Recovery

Figure 3:
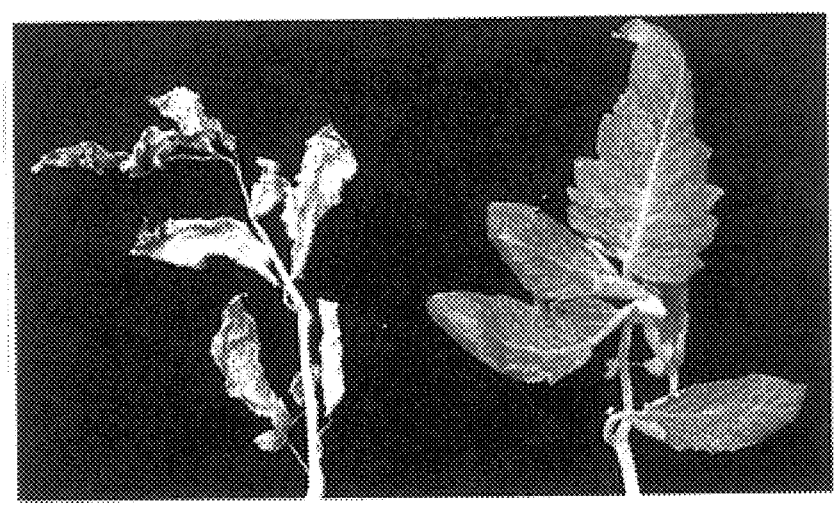
FIG. 3 shows the vigorous shoot growth in plants treated with either LPE 18:1 or LPI as compared to plants treated with water (control) 10 days after spraying with a pesticide.

Marathon with active gradient of imidacloprid (available from Olympic Chemical Co., PO Box K, Mainland, Pa.) is a pesticide used for controlling whitefly in plants. This is a systemic pesticide and is introduced to the plant via soil application. As the pesticide accumulates in the foliage the insects feeding on the plants are killed. Sometimes as this chemical accumulates in the plant it can result in phytotoxicity to the plant. To test this, tomato plants cv. H9144 (cultivar of Heinz Co.) were grown for two (2) months in 20 liter pots in a greenhouse. Seven days after the pesticide Marathon was introduced into the soil in powder form onto the pots, the plants showed leaf damage caused by this pesticide. Many leaves lost chlorophyll and plants had poor shoot growth. Three weeks after the treatment of pesticide, LPEegg, LPE18:1 or LPI (200 mg/L each) solution containing 1% ethanol were sprayed to the point that solution started to run off the leaves. Control plants were sprayed with distilled water containing 1% ethanol. The LPE solution was prepared by wetting 200 mg of LPE in 1 ml ethanol and then adding distilled water to make 1 liter of total volume. The LPE solution was then sonicated 1 minute before spraying. While control plants continued to have poor shoot growth, plants sprayed with lysophospholipids such as LPEegg, LPE18:1, and LPI resumed shoot growth within 4–5 days after spraying. FIG. 3 is a photograph showing vigorous shoot growth in LPE18:1 or LPI-sprayed plants 10 days after spraying, compared to poor shoot growth in the plants sprayed with water (control).

EXAMPLE 4

Protection of Wound-damage and Enhancement of Recovery

Figure 4:
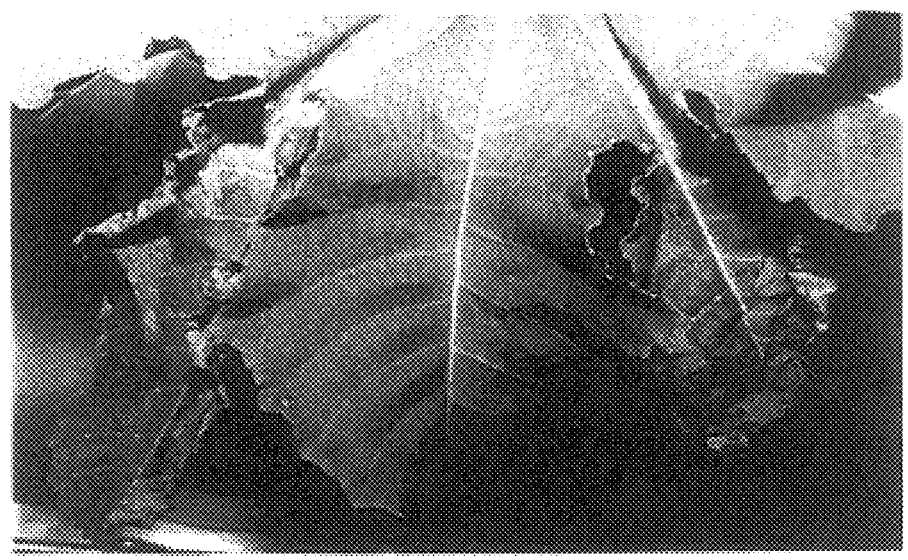
FIG. 4 shows the protection of castor bean seedlings from wound-damage be spray application of LPE as compared to plants sprayed with water (control).

Many insects cause wounding of plants. Studies aimed at simulating insect damage commonly use pliers to cause wounding of plants. For example, in a recent study, this technique was used for castor bean leaves (Ryu, S. B. et al., *Biochimica et Biophysica Acta*, 1393:193–202 (1998). Coatless castor bean (*Ricinus communis L*. cv Hale) seeds were germinated in the dark in moist vermiculite for 3 days. The seedlings were individually transplanted into plastic pots containing a mixture of vermiculite and perlite (1:1, v/v) that were subirrigated with Hoagland nutrient solution (details described in Ryu, S. B. et al., *Biochimica et Biophysica Acta*, 1393:193–202 (1998)). Plants were grown under cool-white fluorescent lights at 23±2° C. with a 14 hour photoperiod. Fully expanded leaves from approximately 8-week-old plants were mechanically damaged with pliers, and then right away water or LPEegg (100 mg/L) was sprayed onto the wound areas, respectively. Control (water-sprayed) part of the leaf showed leaf curling-up and the leaves turned brown after 1 day, while LPE-sprayed part showed much less leaf curling and browning (FIG. 4). LPE-sprayed leaves remained turgid for several days. Wound-healing symptoms in LPE-sprayed leaf part were observed (specifically, leaf damaged areas were healed and gained green color).

EXAMPLE 5

Protection of Microbial Infection and Enhancement of Recovery

Smooth bromegrass (*Bromus inermis* Leyss.) plants were grown in 4 liter plastic pots in a greenhouse. Growing conditions and other details were same as described in Example 1a.

Figure 5:
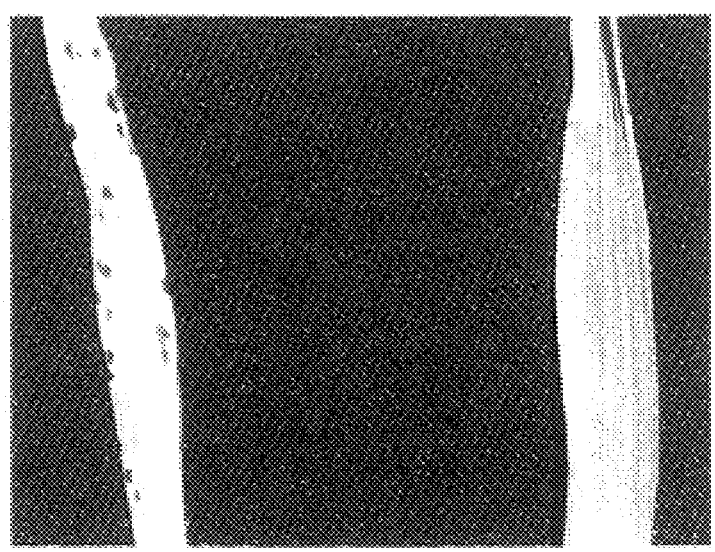
FIG. 5 shows the protection from microbial injury in smooth bromegrass leaf by spray application of LPE and LPI prior to microbial infection.

Water or a mixture of equal parts of LPEegg/LPE18:1/LPI (25 mg/L, respectively) was sprayed on to the plants 1 hour before the spraying of a fungus (*Cochliobolus sativus*) suspension solution. This fungus is known to cause spot blotch or foot (crown) and root rot of temperate cereals and turf grasses (Braverman, S. W., *Bot. Rev.*, 52:1–115 (1986)). Fungus suspension solution was prepared by mixing fungus grown in agar media with distilled water. After a 2 day incubation in a humid chamber, the plants were transferred back to the greenhouse. Three to five days after fungus inoculation, water-sprayed control grass plants showed symptoms of leaf lesions such as purplish brown spots scattered all over areas of the leaves and the leaf damage was apparent even after 2 weeks. In contrast, LPE and LPI mixture-sprayed plants showed less fungus infection symptom and the leaf damage was dramatically healed in 2 weeks (see the photograph in FIG. 5 which was taken 12 days after fungus inoculation).

EXAMPLE 6

Enhanced Germination of Sweet Corn Seeds

Sweet corn seeds (SS Jubilee, certified seed obtained from the Wisconsin Crop Improvement Association, Madison Wis.) were soaked for 2 hours in LPE solution. Seeds were removed from the LPE solution and 50 seeds were placed on 2 paper towels and wetted with distilled water (5 seeds in one row) then seeds were covered with another wet paper towel. The three towels with the seeds were rolled, placed in a metal container and incubated at 25° C. The container was covered with plastic and the cover secured with a rubber band. The germination percentage was tested after 4 and 7 days. The procedure was as specified by the Association of Official Seed Analysts. Four replications were conducted with 50 seeds in each replication. The results are shown below in Table 2. These results show that soaking the seeds in LPE solution, especially at 5 and 10 ppm concentrations, dramatically increased the numbers of seeds that germinated. Furthermore, LPE treated seeds produced larger (root and shoot) seedlings.

TABLE 2

|  | % Germination* | | Average Fresh Mass Produced from 50 seeds | |
| --- | --- | --- | --- | --- |
| Treatments | After 4 days | After 7 days | Root**(g) | Shoot(g) |
| Water | 53.5 ± 1.3 | 57.5 ± 1.3 | 1.0 ± 0.1 | 7.6 ± 0.3 |
| LPE (5 ppm) | 61.0 ± 1.7 | 70.0 ± 2.2 | 1.6 ± 0.4 | 10.0 ± 0.5 |
| LPE (10 ppm) | 69.0 ± 2.6 | 71.5 ± 2.8 | 1.3 ± 0.1 | 8.7 ± 0.2 |
| LPE (20 ppm) | 60.0 ± 3.6 | 65.0 ± 1.3 | 1.2 ± 0.0 | 10.4 ± 0.4 |

*Mean ± SE. (Average of four replications, each replication contained 50 seeds)
**Primary + secondary roots.

EXAMPLE 7

Enhance Germination of 'SS Jubilee' Sweet Corn Seeds

SS Jubilee sweet corn seeds were soaked for 2 hours in LPE solution. Seeds were incubated using the same procedure described in Example 6. The germination percentage was tested after 4 and 7 days. Four replications were conducted with 50 seeds in each replication. The results are shown below in Table 3. Again, as in example 6, LPE (10 ppm) treated seeds showed better germination and gave more robust (larger size) plants. On a commercial level, this means that LPE treatment of the seeds will insure more plants in a given field and that LPE treated seeds will produce plants having a head start.

TABLE 3

| Treatments | % Germination* | | Average Fresh Mass** Produced from 50 seeds | |
|---|---|---|---|---|
| | After 4 days | After 7 days | Root**(g) | Shoot(g) |
| Water | 58.0 ± 2.4 | 63.0 ± 1.8 | 0.8 ± 0.2 | 7.8 ± 0.5 |
| LPE (1 ppm) | 68.5 ± 4.0 | 76.5 ± 4.6 | 0.9 ± 0.1 | 9.1 ± 0.8 |
| LPE (10 ppm) | 61.5 ± 5.7 | 68.0 ± 3.4 | 0.8 ± 0.0 | 7.6 ± 0.3 |
| LPE (10 ppm) | 73.8 ± 2.8 | 78.0 ± 2.3 | 1.1 ± 0.1 | 10.4 ± 0.4 |

**Mean of 40 separate measurements
***Primary + secondary roots
*Mean + SE (Average of four replications, 50 seeds in each replication)

EXAMPLE 8

Enhanced Germination of H.2350 Field Corn Seeds

H.2350 (Certified seed obtained from the Wisconsin Crop Improvement Association, Madison, Wis.) field corn seeds were soaked in LPE solution. Seeds were incubated at 25° C. for 8 days using the procedure described in Example 6. Four replications were conducted with 50 seeds in each replication. The results are shown below in Table 4. As with the sweet corn (SS Jublilee), LPE treatment of field corn seed improved seed germination (although even the water treated seeds demonstrated good germination) as well as improved the size of seedling.

TABLE 4

| Treatments | % Germination* | Fresh Weight** | |
|---|---|---|---|
| | | Root***(g) | Shoot (g) |
| Water | 93.0 ± 1.0 | 12.7 ± 0.3 | 14.4 ± 0.2 |
| LPE (5 ppm) | 97.0 ± 0.6 | 14.2 ± 0.8 | 16.2 ± 0.6 |
| LPE (10 ppm) | 98.5 ± 1.0 | 13.6 ± 0.3 | 15.6 ± 0.7 |

*Mean ± SE (Average of four replications, 50 seeds in each replication)
**Average mass produced from 50 seeds
***Primary + secondary roots.

EXAMPLE 9

Enhanced Germination of 'Hazel' Oats

'Hazel' oats (Certified seed obtained from the Wisconsin Crop Improvement Association, Madison, Wis.) were soaked in LPE or LPC. Seeds were soaked for either 30 minutes or 2 hours at room temperature (23±2° C.) and then incubated at 20° C. using the official seed germination test rules (Rules for testing seeds are published by the Association of Official Seed Analysts) for testing seeds. Four replications were conducted with 100 seeds in each replication. Results are shown below in Table 5. The results show that soaking seeds in LPE (10 ppm) or LPE and LPC (10 ppm each) increases the percentage of seeds germinated. Moreover, a greater proportion of the seeds treated with these lipids, germinated earlier. Thus, this seed treating increased both the rate and amount of seed germination.

TABLE 5

| | % Germination (Mean ± SE) | | | |
|---|---|---|---|---|
| | After 4 days | | After 10 days | |
| Treatments | 30 min | 2 hours | 30 min. | 2 hours |
| Water | 75.5 ± 1.9 | 75.5 ± 3.7 | 83.0 ± 1.6 | 87.3 ± 4.0 |
| LPE (10 ppm) | 87.7 ± 0.9 | 82.8 ± 1.1 | 91.3 ± 0.7 | 94.3 ± 1.3 |
| LPE (10 ppm) | 82.5 ± 1.7 | 82.0 ± 1.2 | 90.8 ± 1.1 | 93.5 ± 1.0 |
| LPE + LPC (10 ppm each) | 85.5 ± 1.7 | 84.5 ± 1.7 | 92.0 ± 2.0 | 96.3 ± 0.5 |

EXAMPLE 10

Enhanced Germination of 'Hazel' Oats

'Hazel' oat seeds were soaked in LPE or LPC for 30 minutes at room temperature (23±2° C.), then incubated at 20° C. to evaluate the influence on seedling vigour parameters (Root fresh weight and shoot fresh weight). Values are mean±SE (4 replications). Results are shown below in Table 6. Seeds treated with LPE (10 ppm) had higher root and shoot fresh weight. Thus, LPE treatment increased seedling vigor.

TABLE 6

| Treatment | Root fresh wt per seedling (mg) | Shoot Fresh wt per seedling (mg) |
|---|---|---|
| Water | 40.7 ± 3.0 | 121.8 ± 6.8 |
| LPE (10 ppm) | 48.4 ± 1.9 | 124.1 ± 3.0 |
| LPC (10 ppm) | 40.4 ± 2.7 | 108.9 ± 4.5 |
| LPE + LPC (10 ppm each) | 43.1 ± 2.5 | 115.0 ± 5.5 |

EXAMPLE 11

Enhanced Germination of 'Hazel Oats'

'Hazel' oat seeds were soaked in LPE or LPC for 2 hours at room temperature (23±° C.), then incubated at 20° C. to evaluate the influence of LPE and LPC or seedling vigour (Root or shoot fresh weight). Values are mean±SE (4 replications). Results are shown below in Table 7. Results show that either LPE or LPC alone or in combination increased both root and shoot fresh weight. Thus, two hour soaking in lipids resulted in enhanced seedling vigor.

TABLE 7

| Treatments | Root fresh wt per seedlings (mg) | Shoot Fresh wt per seedlings (mg) |
|---|---|---|
| Water | 41.1 ± 1.2 | 117.6 ± 6.0 |
| LPE (10 ppm) | 46.4 ± 0.6 | 121.1 ± 2.5 |
| LPC (10 ppm) | 48.9 ± 0.7 | 130.4 ± 2.7 |
| LPE + LPC (10 ppm each) | 48.8 ± 2.3 | 120.8 ± 2.1 |

All references referred to herein are incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. A method of protecting a plant or a seed from a stress injury, the method comprising the step of applying to a plant or seed in need of protection from a stress injury, an effective amount of a composition comprising at least one lysophospholipid having the formula:

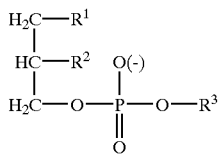

wherein $R^1$ is selected from the group consisting of $C_5$–$C_{22}$ acyloxy and $C_5$–$C_{22}$ alkoxy group; $R^2$ is selected from the group consisting of hydrogen, hydroxyl, $C_1$–$C_5$ acyloxy and $C_1$–$C_5$ alkoxy group; and $R^3$ is selected from the group consisting of hydrogen, choline, ethanolamine, glycerol, inositol and serine, wherein $R^1$ and $R^2$ are interchangeable.

2. The method of claim 1 wherein the composition further comprises at least one activating agent.

3. The method of claim 1 wherein the lysophospholipid is lysophosphatidylethanolamine, lysophosphatidylinositol or combinations thereof.

4. The method of claim 1 wherein the composition is an aqueous solution.

5. The method of claim 1 wherein the composition is applied onto the plant or seed before exposure to the stress injury.

6. The method of claim 1 wherein the composition contains from about 5.0 to about 500 mg per liter of lysophospholipid.

7. The method of claim 2 wherein the activating agent is ethanol, a nonylphenol polyoxyethylene ether or a siloxylated polyether.

8. The method of claim 1 wherein the stress injury is the result of an abiotic or a biotic stress.

9. The method of claim 8 wherein the abiotic stress is the result of chilling, freezing, wind, drought, heat, chemicals or imbibation.

10. The method of claim 9 wherein the chemical is a pesticide or herbicide.

11. The method of claim 8 wherein the abiotic stress is imbibation during germination of a seed.

12. The method of claim 8 wherein the biotic stress is the result of infection by an insect, nematode or pathogen.

13. The method of claim 12 wherein the pathogen is a fungus, bacteria or virus.

14. A method of enhancing the recovery of an injured plant from a stress related injury, the method comprising the step of applying to the injured plant an effective amount of a composition comprising at least one lysophospholipid having the formula:

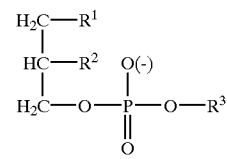

where $R^1$ is selected from the group consisting of $C_5$–$C_{22}$ acyloxy and $C_5$–$C_{22}$ alkoxy group; $R^2$ is selected from the group consisting of hydrogen, hydroxyl, $C_1$–$C_5$ acyloxy and $C_1$–$C_5$ alkoxy group; and $R^3$ is selected from the group consisting of hydrogen, choline, ethanolamine, glycerol, inositol and serine, wherein $R_1$ and $R_2$ are interchangeable.

15. The method of claim 14 wherein the composition further comprises at least one activating agent.

16. The method of claim 14 wherein the lysophospholipid is lysophosphatidylethanolamine, lysophosphatidylinositol, lysophosphatidylcholine or combinations thereof.

17. The method of claim 14 wherein the composition is an aqueous solution.

18. The method of claim 14 wherein the composition is sprayed onto the plant after exposure to a stress injury.

19. The method of claim 18 wherein the stress injury is the result of an abiotic or a biotic stress.

20. The method of claim 19 wherein the abiotic stress is the result of chilling, freezing, wind, drought, heat, chemicals or imbibation.

21. The method of claim 20 wherein the chemical is a pesticide or a herbicide.

22. The method of claim 19 wherein the biotic stress is the result of infection by an insect, nematode or pathogen.

23. The method of claim 22 wherein the pathogen is a fungus, bacteria or virus.

24. The method of claim 14 wherein the composition contains from about 5.0 to about 500 mg per liter of lysophospholipid.

25. The method of claim 15 wherein the activating agent is ethanol, a nonylphenol polyoxyethylene ether or a siloxylated polyether.

* * * * *